United States Patent [19]
Hess

[11] Patent Number: 5,066,298
[45] Date of Patent: Nov. 19, 1991

[54] ARTICLE AND METHOD OF SHEATHING ANGIOPLASTY BALLOONS

[75] Inventor: Robert L. Hess, Portola Valley, Calif.

[73] Assignee: Progressive Angioplasty Systems, Inc., Menlo Park, Calif.

[21] Appl. No.: 443,393

[22] Filed: Nov. 30, 1989

[51] Int. Cl.⁵ .......................................... A61M 29/02
[52] U.S. Cl. ..................................... 606/194; 604/96
[58] Field of Search ............... 606/194, 192, 193, 196; 604/96

[56] References Cited

U.S. PATENT DOCUMENTS

| | | | |
|---|---|---|---|
| 4,141,364 | 2/1979 | Schultze | 128/4 X |
| 4,261,339 | 4/1981 | Hanson et al. | 600/18 |
| 4,563,176 | 1/1986 | Gustavsson et al. | 604/163 |
| 4,710,181 | 12/1987 | Fuqua | 604/280 |
| 4,738,666 | 4/1988 | Fuqua | 604/280 |

Primary Examiner—Michael H. Thaler
Attorney, Agent, or Firm—Burns, Doane, Swecker & Mathis

[57] ABSTRACT

A pre-compressed angioplasty balloon catheter and method of manufacture wherein the balloon portion of the catheter is wrapped for storage and for minimizing its outside diameter for purpose of insertion into the body.

12 Claims, 1 Drawing Sheet

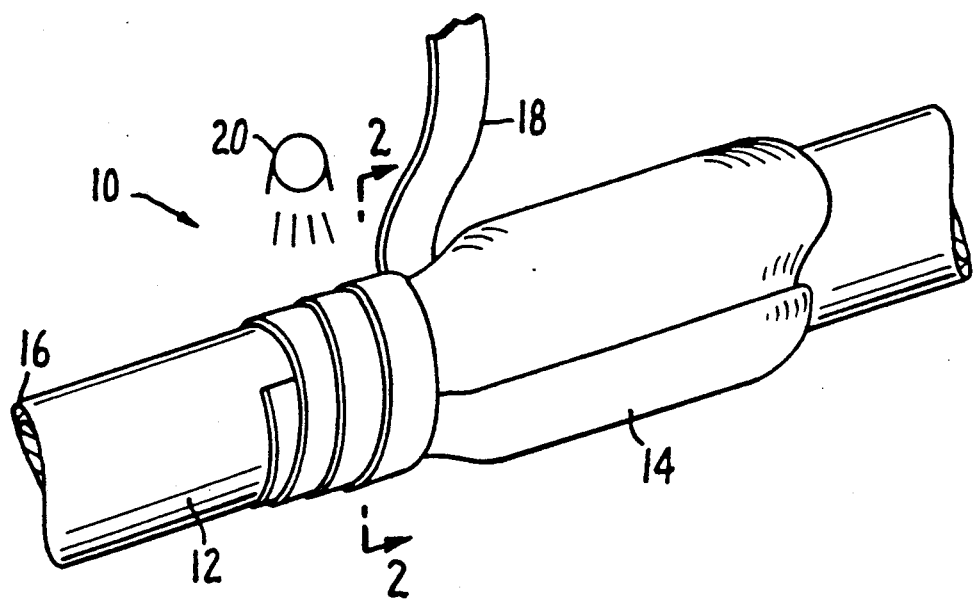
FIG. 1.
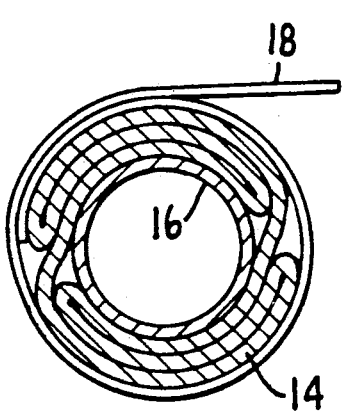 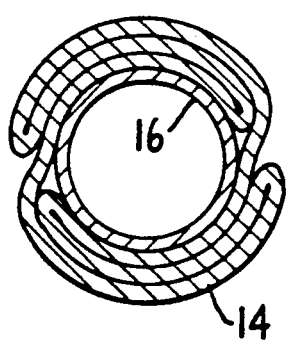 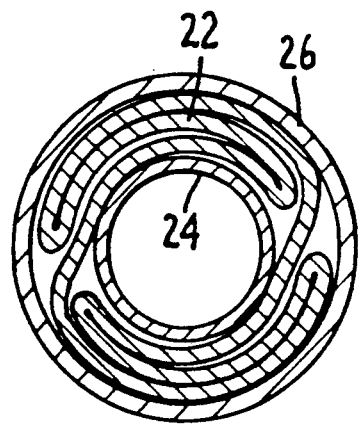
FIG. 2  FIG. 3  (PRIOR ART) FIG. 4.

ARTICLE AND METHOD OF SHEATHING ANGIOPLASTY BALLOONS

BACKGROUND OF THE INVENTION

1. Field of the Invention

The present invention is directed to angioplasty catheters and specifically to the sheathing of such catheters.

2. Description of the Prior Art

Balloons on dilation catheters are provided with a sheath to protect the balloon prior to use and, more importantly, to "cold flow" the balloon material into a low collapsed profile. Closely fitted pieces of tubing made from low friction material such as tetrafluoroethylene (TFE) have been used for this purpose. These tubes, however, have several disadvantages.

First, the tube must be pushed over the length (2-3 cm.) of the balloon portion of the catheter without damaging the balloon. Although the balloon portion is visually inspected before insertion into the body, any weakening of the balloon wall will be detected only upon inflation of the balloon within the patient.

Second, clearance must be provided in order to avoid damage. The greater the clearance between the collapsed balloon profile and the inside of the tube, the greater the eventual diameter of the collapsed balloon due to progressive "cold flow" of the balloon material in storage. In addition to the sliding clearance needed, the tube has a manufacturing tolerance of, for example, at least plus or minus 0.001 inch. In a low profile balloon having a minimum collapsed diameter of 0.030 inch where a minimum sliding clearance of 0.001 inch is required, the tube with a manufacturing tolerance will cause the desired profile to vary by as much as 0.003 inch, i.e., ten percent of the minimum collapsed diameter of the balloon. If one further allows a tolerance for catheter components that can vary, the variance from the desired profile can be even greater.

During the time in which the balloon portion resides within the outer tubing or sheath, the balloon portion will take a set, i.e., its material will "cold flow", and the outside diameter of the collapsed balloon portion will approximate the inside diameter of the outer tube. The smaller the outer diameter of the balloon portion of the catheter, the smaller the critical artery location into which it may be inserted. It would be advantageous for angioplasty procedures to have a more compact collapsed profile than that which conventionally results from the tubing arrangement discussed above.

U.S Pat. Nos. 4,710,181 and 4,738,666 disclose variable diameter catheters which are folded in order to reduce the diameter for convenience and for less traumatic insertion into a body orifice. In these devices, the catheter is maintained in a compressed condition by means of the external sheath which is removed after the catheter is placed in the body orifice. In angioplasty devices, the use of an outer sheath within the body requires an even greater opening size to accommodate the dimensions of the sheath. It would be beneficial to have some method of compacting a collapsed angioplasty balloon other than by compressing it and inserting it into a sheath with a fixed dimension which then must also be inserted into the body.

U.S. Pat. No. 4,563,176 discloses the use of a flexible protective sheath in the form of a plastic bag which encloses a catheter as a sterile storage device. The sheath is removed before insertion of the catheter, but, unfortunately, does not compact the catheter to a minimum insertion profile. It would be beneficial to have a method of compacting a collapsed angioplasty balloon portion of a catheter both for eventual insertion and for maintaining the device for storage purposes.

SUMMARY OF THE INVENTION

The purpose of the invention is to minimize the outside diameter of an angioplasty balloon catheter for purposes of insertion into the body. To accomplish this purpose there is provided a catheter made by the following steps: collapsing the balloon portion of an angioplasty catheter, winding a protective wrapping around the collapsed portion to thereby compress the portion to a smaller diameter, and then preferably setting the compressed, collapsed balloon portion such that such portion will maintain its minimum dimension upon removal of the sheath before inflation of that portion.

In one aspect of the invention there is provided a method of sheathing an angioplasty balloon comprising the steps of:

providing an angioplasty catheter having a body portion and a balloon portion, the balloon portion being larger in diameter than the body portion;

collapsing the balloon portion to a low profile;

supporting the circumference of the balloon portion of the catheter;

wrapping the circumference of the balloon portion of the catheter tightly radially inwardly while supporting the balloon portion of the catheter to compress said portion to a smaller diameter; and setting the wrapped balloon portion of the catheter to its compressed diameter.

In another aspect of the invention there is provided a catheter comprising:

a body portion;

a balloon portion, said balloon portion being larger in diameter than the body portion; and a circumferential wrap over said balloon portion, said wrap diametrically compressing said balloon portion radially inwardly, said balloon portion being set in said compressed diameter, said wrap sheathing said catheter during storage, said balloon portion remaining substantially diametrically compressed when said wrap is removed for the purpose of insertion into the body.

DESCRIPTION OF THE DRAWING

FIG. 1 is a partial perspective view of a catheter according to the invention wherein the balloon portion of the catheter is being wound by a tape to compress and protect that portion.

FIG. 2 is an enlarged cross-sectional view taken along section line 2—2 in FIG. 1 illustrating the compacted portion of the catheter.

FIG. 3 is a view similar to FIG. 2 of the balloon portion with the wrapping removed.

FIG. 4 is a figure similar to FIG. 2 illustrating a sheath used to protect a balloon catheter according to the prior art.

DESCRIPTION OF THE PREFERRED EMBODIMENT

With continued reference to the drawing, FIG. 1 illustrates an angioplasty catheter, shown generally at 10, having a body portion 12, a balloon portion 14, and an inner tube 16. Balloon portion 14 is shown collapsed, although it is understood that balloon portion 14 may be expanded in a conventional manner by the supply of fluid to balloon portion 14 through the annular area between inner tube 16 and body portion 12. In its collapsed state, balloon portion 14 folds down into close proximity with the outside surface of inner tube 16.

Although a co-axial catheter construction is shown, it is understood that it is within the scope of the invention to sheath other catheter constructions such as multi-lumen, balloon-on-wire, monorail type, and catheters using positioning balloons such as some types of atherectomy and laser angioplasty catheters, etc., wherein the inner tube may vary or not even exist.

According to the method of the present invention, balloon portion 14 of angioplasty catheter 10 is collapsed to a low profile and is tightly wrapped in its collapsed condition with tape 18. Tape 18 may be wrapped in conventional overlapping fashion to both compress balloon portion 14 and to form a sheath which seals and protects that portion of the catheter during storage. The compression of balloon portion 14 by tape 18 is clearly shown in FIG. 2.

Tape 18 is preferably made from TFE. Other materials and cross-sections, including round filament, are considered to be within the scope of the invention. Such tapes or filaments can be made of almost any polymer or natural fiber or metal with sufficient strength and ductility.

In order to insure uniformity of diameter, it is important to support the circumference of balloon portion 14 during winding. Support is provided by inner tube 16. Further or alternative support can be provided by insertion of a mandrel within inner tube 16. Various configurations of mandrels are within the scope of the invention, depending upon the catheter construction.

It is also within the scope of the invention to support balloon portion 14 in its collapsed dimension by pressuring inner tube 16 with air or a fluid. In addition, it is within the scope of the invention to support balloon portion 14 externally by means of a travelling support wherein the wrap is applied between two closely spaced supports which travel along the outside length of the wrapped area as the wrap is being applied.

According to the method of the invention, the wrapped portion is preferably subsequently heated, such as by exposure to a heating source 20, as symbolically shown in FIG. 1. It is understood that the long-term storage of balloon portion 14 in its compressed condition will create some type of "cold flow" set condition in the material without the use of additional heat. It is, however, preferred that an additional positive step be taken to further condition the compressed balloon portion 14 while it is wrapped. As a result of the wrapping and setting, tape 18 may be removed prior to insertion of the catheter, and balloon portion 14 will remain substantially compressed prior to inflation. The retention of the compressed diameter can be seen in FIG. 3 where the tape has been removed.

FIG. 4 illustrates the protection of balloon portion 22 of the catheter by conventional means wherein balloon portion 22 has been collapsed on top of inner tube 24 and then inserted into tube 26 for purposes of storage. It can be seen that the storage of catheters in this fashion has several disadvantages, as discussed earlier. Tube 26 must be pushed along the length of balloon portion 22 of the catheter. Such movement can damage the catheter. Therefore, some clearance must be provided. Any tolerance will result in a larger diameter space in which balloon portion 22 will remain during storage and into which the balloon portion will move and conform by the "cold flow" of the material. The final result is a larger diameter balloon profile upon removal of the sheath than the profile accomplished by the present invention.

Although the present invention has been described with reference to the preferred embodiment, it is understood that modifications and variations may be resorted to without departing from the spirit and scope of the invention, as those skilled in the art will readily understand.

What is claimed is:

1. A method of sheathing an angioplasty balloon comprising the steps of:
    providing an angioplasty catheter having a body portion and a balloon portion, the balloon portion being larger in diameter than the body portion;
    collapsing the balloon portion to a low profile and supporting the inside circumference of the balloon portion of the catheter in its low profile;
    wrapping the circumference of the balloon portion of the catheter tightly radially inwardly with a separate helical wrap while supporting the balloon portion of the catheter compressing said balloon portion to a smaller diameter than said low profile; and
    producing a set in the wrapped balloon portion of the catheter in its compressed smaller diameter, said balloon portion remaining substantially compressed in its smaller diameter upon removal of said wrap.

2. A method as in claim 1 wherein the circumference of the inside balloon portion is supported by inserting a mandrel within said balloon portion of the catheter.

3. A method as in claim 1 including the step of providing an inner tube within said angioplasty catheter, said tube extending throughout the body portion and the balloon portion of the catheter.

4. A method as in claim 3 wherein said inner tube supports the inside circumference of the balloon portion during the wrapping of the circumference of the balloon portion.

5. A method as in claim 4 including the further step of supporting the inner tube of the catheter.

6. A method as in claim 5 wherein the inner tube is supported by inserting a mandrel within said inner tube.

7. A method as in claim 5 wherein the inside circumference of the inner tube is supported by pressurizing said inner tube while wrapping the circumference of the balloon portion.

8. A method as in claim 1 wherein the circumference of the balloon portion is supported externally.

9. A method as in claim 1 wherein a continuous tape is used to wrap in overlapped fashion.

10. A method as in claim 1 wherein a continuous filament is used to wrap.

11. A method as in claim 1 wherein said setting includes heating the wrapped balloon portion.

12. A catheter comprising:
    a body portion;
    a balloon portion, said balloon portion being larger in diameter than said body portion; and
    a circumferential, generally helical wrap over said balloon portion, said wrap diametrically compressing said balloon portion radially inwardly, said balloon portion being set in said compressed diameter, said wrap sheathing said catheter during storage, said balloon portion being set and remaining substantially diametrically compressed when said wrap is removed for the purpose of insertion into the body.

* * * * *

UNITED STATES PATENT AND TRADEMARK OFFICE
CERTIFICATE OF CORRECTION

PATENT NO. : 5,066,298
DATED : November 19, 1991
INVENTOR(S) : Robert L. Hess

It is certified that error appears in the above-identified patent and that said Letters Patent is hereby corrected as shown below:

Column 4, line 28 (Claim 2, line 1), following "the" insert --inside--.

Column 4, line 29 (Claim 2, line 2), delete "inside".

Column 4, line 49 (Claim 9, line 1), following "continuous" insert --flat--.

Signed and Sealed this

Thirteenth Day of April, 1993

Attest:

STEPHEN G. KUNIN

*Attesting Officer*  *Acting Commissioner of Patents and Trademarks*